US00PP34503P2

(12) United States Plant Patent
Hansen

(10) Patent No.: US PP34,503 P2
(45) Date of Patent: Aug. 16, 2022

(54) ***DIANTHUS* PLANT NAMED 'PAINT THE TOWN FANCY'**

(50) Latin Name: ***Dianthus* hybrid**
Varietal Denomination: 'Paint the Town Fancy'

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,290

(22) Filed: Dec. 18, 2020

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./273, 276, 277
CPC ... A01H 5/02; A01H 5/00; A01H 6/30; A01H 6/305; A01H 6/1424
See application file for complete search history.

(56) References Cited

U.S. PATENT DOCUMENTS

PP14,549 P3 * 2/2004 Whetman ..... A01H 6/305 Plt./282
PP29,222 P2 * 4/2018 Hansen ..... A01H 5/02 Plt./272

OTHER PUBLICATIONS

Digger Magazine Farwest New Varieties Showcase 2020, retrieved on Apr. 5, 2021, retrieved from the Internet at http://www.diggermagazine.com/wp-content/uploads/2020/08/New-Varieties-2020-Final.pdf, pp. 34-48. (Year: 2020).*

* cited by examiner

*Primary Examiner* — June Hwu

(57) ABSTRACT

A new and unique plant cultivar of perennial carnation or pinks, *Dianthus* plant named 'Paint the Town Fancy' with numerous, single, lightly-sweet fragrant flowers producing a full rounded face. Each flower has five overlapping petals that are rosy-fuchsia colored with darker red bar in the center. Petals have coarsely dentate apices. Flowering season is strong for four weeks beginning in late spring and continues less densely to mid-fall. The habit is compact and dense with glaucous blue-green foliage.

1 Drawing Sheet

Botanical denomination: *Dianthus* hybrid.
Cultivar designation: 'Paint the Town Fancy'.

STATEMENT REGARDING PRIOR DISCLOSURES UNDER 37 CFR 1.77(B)(6)

The first non-enabling disclosure of the claimed plant was made by Walters Gardens, Inc. on Dec. 1, 2019 in the form of a website brief description and photograph followed by a short description and photograph in the "Walters Gardens 20-21 Catalog" by Walters Gardens, Inc. The first sales of the claimed plant was on Jun. 29, 2020 by Walters Gardens, Inc. to Walla Walla Nursery Co. Walters Gardens, Inc. obtained the new plant and information about the new plant directly from the inventor. No plants of *Dianthus* 'Paint the Town Fancy' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Paint the Town Fancy'. The new plant was the result of an intentional cross on Oct. 12, 2014 under the direction of the inventor between the proprietary, unreleased, unnamed hybrid known only by the breeder code 12-43-1 (not patented) as the female or seed parent and the male or pollen parent is the proprietary, unreleased, unnamed hybrid known only by the breeder code 12-47-4 (not patented). The cross was harvested and sown in the winter of 2015. The new hybrid was first selected from trials at a wholesale perennial nursery in Zeeland, Mich. during the summer of 2017 as a single seedling clone and given the breeder code number 14-33-5 later in the evaluation processes. *Dianthus* 'Paint the Town Fancy' has been asexually propagated at the same nursery in Zeeland, Mich. since 2017 using traditional shoot tip cutting procedures and later sterile shoot-tip tissue culture and found to reproduce plants that are identical and exhibit all the characteristics of the original plant in successive generations.

SUMMARY OF THE INVENTION

*Dianthus* 'Paint the Town Fancy' has not been evaluated under all possible environmental conditions. The phenotype may vary with variations in environment including: growing temperature, available sunlight, nutrients, water, etc. without a change in the genotype of the plant.

The closest comparison plants to the new plant known to the inventor include: 'Paint the Town Magenta' U.S. Plant Pat. No. 29,222, 'Paint the Town Fuchsia' U.S. Plant Pat. No. 28,636, KAHORI® 'Pink' (not patented) and 'Paint the Town Red' U.S. Plant Pat. No. 33,293.

'Paint the Town Magenta' has a similar habit and foliage but the flowers are slightly smaller and of vibrant magenta-pink, and does not have the dark red bar. 'Paint the Town Fuchsia' has similar habit and foliage, but the flowers are slightly smaller and fuchsia colored with lavender centers. 'Kahori' has smaller habit with more light green foliage and the flowers are more pinkish without the dark red bar. 'Paint the Town Red' has similar habit and foliage and the flowers are more reddish colored with a smaller dark eye. 'Neon Star' U.S. Plant Pat. No. 14,549 has a larger habit in side-by-side growing trials at the same age, and flowers that are darker red with the identical dark-red colored center without an obvious eye. The female parent, 12-43-1, had a pinkish flower with a dark red bar, but was not saved as a plant and there is no photographic record for further comparison. The male parent, 12-47-4, had a dark red without the dark red eye.

*Dianthus* 'Paint the Town Fancy' is distinct from its parents and all other *Dianthus* known to the applicant in the following combined traits:

1. Single flowers with five overlapping petals forming a full rounded face;
2. Petals have a coarsely serrated apex;
3. Petal color is a rosy-fuchsia with a dark red center bar;
4. Numerous flowers per plant on heavily branched upright stems;
5. Prolonged flowering period with a strong flush in late spring and continuing to mid-fall;
6. Compact habit and dense, glaucous, blue-green foliage.

BRIEF DESCRIPTION OF THE DRAWINGS

The photographs of 'Paint the Town Fancy' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
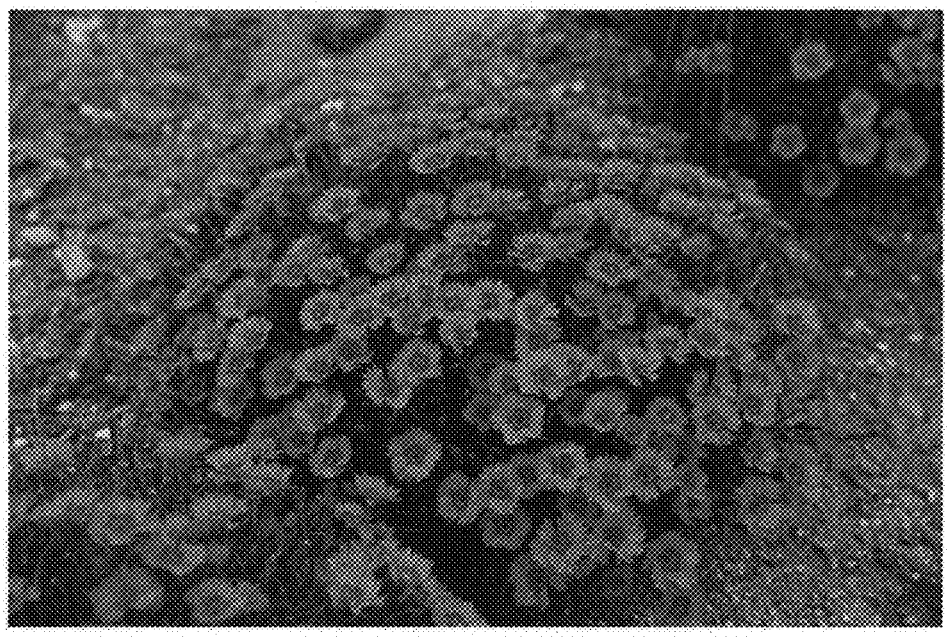
FIG. 1 shows the habit of the plant in mid-season flowering.
Figure 2:
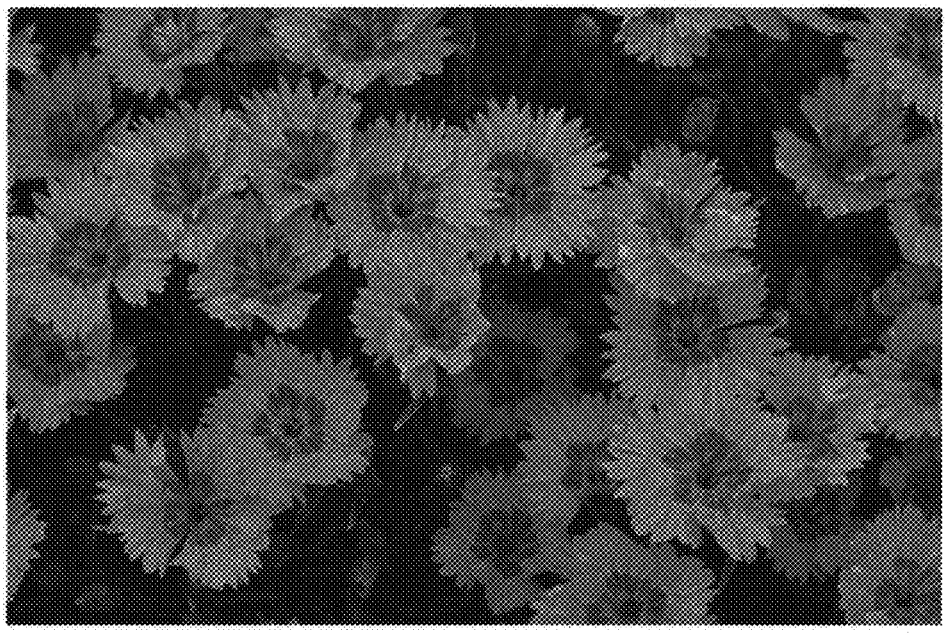
FIG. 2 shows a close-up of the flowers and buds.

The following detailed description of 'Paint the Town Fancy' is based on observations of two-year-old plants in a full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 12-43-1; the male or pollen parent is 12-47-4;

Plant habit: Caespitose, herbaceous, evergreen, winter-hardy perennial; stems and peduncles highly branched, mostly erect stems to slightly arching; height of foliage about 15.0 cm and about 47.0 cm across; height in flower is about 18.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to micro-serrulate; apex narrowly acute; base truncate, decurrent, clasping; straight; no fragrance detected; glaucosity medium.

*Leaf dimensions*.—To about 35.0 mm long and about 4.0 mm wide near middle, average about 30.0 cm long and 4.0 mm wide.

*Leaf color*.—Young expanding and mature leaves adaxial and abaxial blend nearest RHS N138B.

*Venation*.—Not pronounced; obscurely pinnate, coloration same as that of leaf top and bottom.

Stems: About 100 per plant; upright; cylindrical, hollow; glabrous; glaucous; branching in upper nodes;

*Stem size*.—About 16.0 cm long to peduncle and about 2.5 mm wide at base.

*Stem color*.—Between RHS 177D and RHS 195B.

*Branching*.—Numerous; typically alternate from lower nodes; about 12 per main stem and about 200 per plant in late spring peak; branch size average about 3.5 cm long and 1.0 mm diameter at time of initial flowering.

*Nodes*.—About 4.0 mm across; color nearest RHS 177D.

*Internodes*.—About 10 to 12 per stem before peduncle; average about 2.1 cm apart depending on growing temperature, shorter in cooler conditions.

*Inflorescence*.—Flowering in the upper 4.0 cm and to about 8.8 cm across; with an average of two flowers per inflorescence.

*Flower bud*.—Slowly opening; glabrous; glaucous; with calyx still closed: cylindrical with attenuate base and rounded apex; about 25.0 mm long and 4.0 mm across; without extrusion of styles.

*Flower bud color*.—With petals extended beyond calyx petal portion nearest RHS 72A; calyx proximally between RHS 138A and RHS 147B and proximally moderately tinted nearest RHS 187B.

Flower:

*Type*.—Terminal, cymose; perfect; salverform; actinomophic; single.

*Attitude*.—Upright to slightly outwardly around perimeter of plant.

*Dimension*.—About 3.1 cm across and extending about 3.2 cm above base of calyx tube and 5.5 mm wide at apex of calyx.

*Flowers per stem*.—Up to 3, average 2.

*Pedicel*.—Glaucous, glabrous, cylindrical, stiff; primarily upright; short.

*Pedicel size*.—To about 2.0 mm long and about 1.5 mm diameter.

*Pedicel color*.—Nearest RHS 144A.

*Flower period*.—Beginning mid-May with a strong flush for about four weeks and continuing more sparsely through mid-fall.

*Flower fragrance*.—Lightly sweet.

*Flower lasting quality*.—Individually about seven to ten days on or cut from plant.

*Corolla profile*.—Lower part flat; upper portion flat to convex.

*Petals*.—Five; glabrous adaxial and abaxial except at base of adaxial limb puberulent; consisting of a rounded limb and a claw; limb trapezoidal and limb and claw combined are flabellate; limb apex and margin deeply dentate with many teeth to about 4.0 mm long and 2.0 mm wide at base; limb base attenuate toward claw; claw with attenuate base; bent outwardly at limb base creating a flat rounded face; persistent; having a darker eye.

*Petal dimensions*.—Limb to about 13.0 mm long and 17.0 mm wide; claw about 15.0 mm long and 4.0 mm wide tapering to attenuate base of about 1.0 mm across; whole petal to about 32.0 mm long, average about 31.0 mm long; darker eye about 10 mm across.

*Petal color*.—Young and mature adaxial claw base nearest RHS 145D and distally nearest RHS N74A, young and mature adaxial limb distally nearest RHS N74A with 5.0 mm wide bar stretching at base of limb nearest RHS 71A; young and mature abaxial claw nearest RHS 145D, young and mature abaxial limb base nearest RHS N74C.

*Calyx*.—Tubular; to about 14.0 mm long and 5.0 mm diameter at apex.

*Sepals*.—Five; acute apex and fused in basal 10.0 mm forming five-toothed calyx tube; glabrous adaxial and abaxial; glaucous abaxial; margins entire to micro-ciliolate.

*Sepal size*.—Individually about 14.0 mm long and about 2.0 to 3.0 mm across at fusion.

*Sepal color*.—Adaxial nearest RHS 138C; abaxial nearest RHS 146C with apices strongly blushed to solid RHS 71A and base lightly blushed nearest RHS 71A.

*Peduncle*.—Glabrous; glaucous; hollow, cylindrical; stiff; about 8.0 cm long and about 2.5 mm diameter at base; attitude mostly upright to slightly arching.

*Peduncle color*.—Blend nearest RHS N138B with light glaucous bloom.

*Epicalyx*.—Two pairs subtending each flower; both pairs adpressed; opposite, glaucous, glabrous; sessile, margin entire; ovate to obtuse; inner pair narrowly acute apex and truncate base, 9.0 mm long and about 6.5 mm across near middle; outer pair with very short narrowly acute apex, truncate clasping base, about 8.0 mm long and about 4.5 mm wide.

*Epicalyx color*.—Both pairs variable; adaxial and abaxial margin nearest RHS 145C and remaining middle to apex nearest RHS 141B; no anthocyanin pigment noted.

*Androecium*.—Up to 10; not fully developed. Filaments: straight to about 14 mm long and 0.1 mm diameter; color nearest RHS NN155A; Anther: rudimentary or not observed; oblong; basifixed; about 0.7 mm long and 0.3 mm diameter; color nearest RHS 160C; Pollen: not observed.

*Gynoecium*.—Single; to about 29.0 mm long. Style: bifurcate just above ovary; shoulder absent; to 21.0 mm long and 1.0 mm across; color proximally nearest RHS NN155D, distally between RHS N186C and RHS N186D, hairs proximally nearest RHS 71A and distally nearest RHS N186C; Stigma: slightly flattened abaxial to adaxial; puberulent along adaxial surface; about 1.0 mm long and 0.7 mm wide; color nearest RHS N186C; Ovary: superior; cylindrical; acute apex and truncate base; smooth, lustrous; about 8.0 mm long and 4.0 mm diameter; color distally nearest RHS 145A and proximally nearest RHS 150C.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Paint the Town Fancy' essentially as herein described and illustrated.

* * * * *